United States Patent [19]

Sommer et al.

[11] Patent Number: 4,686,293
[45] Date of Patent: Aug. 11, 1987

[54] CHEMICAL AGENTS

[75] Inventors: Harold Z. Sommer, Havre de Grace; Omer O. Owens, Abingdon, both of Md.

[73] Assignee: The United States of America as represented by the Secretary of the Army, Washington, D.C.

[21] Appl. No.: 643,302

[22] Filed: May 29, 1967

[51] Int. Cl.[4] .................... C07O 213/65; A61K 31/44
[52] U.S. Cl. .................................................. 546/261
[58] Field of Search .................... 260/294 A, 296; 167/46 A, 47; 424/263; 546/261; 514/335

[56] References Cited

U.S. PATENT DOCUMENTS 2,857,390 10/1958 Kirchner .................... 260/294 A
3,188,955 6/1965 Brown .................................. 102/24

Primary Examiner—John F. Terapane
Assistant Examiner—J. E. Thomas
Attorney, Agent, or Firm—Anthony T. Lane; Harold H. Card, Jr.

[57] ABSTRACT

New chemical compounds having the generic formula:

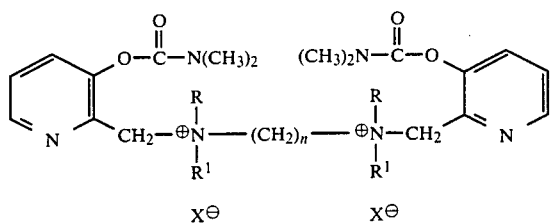

wherein n is 5–16 methylene groups, R, R' are radicals selected from the group consisting of methyl, ethyl, propyl, isopropyl, butyl, benzyl, and x is one equivalent of an anion selected from the group consisting of monovalent and polyvalent anions, and having utility as incapacitating agents and in munitions.

6 Claims, No Drawings

CHEMICAL AGENTS

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces or interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influence association and hydration and may considerably change the solubilities in physiological media. In bis-quaternary and poly-quaternary compounds, the distance between the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields wherein said products are well suited for industrial scale manufacture.

Our compounds may be employed in any munition suitable for handling a relatively non-volatile toxic agent such as bombs, shells, spray tanks, rockets, missiles, aerosol generators, and others.

Other objects of and uses for the invention will in part be obvious and will in part appear hereinafter in the following detailed description thereof.

In accordance with our invention a mixture of an aminocarbamate, such as (3-dimethylcarbamoxy-α-picolinyl)methylethylamine, and an α,ω-dihaloalkane, such as 1,8-dibromooctane, was reacted by either allowing to stand at room temperature for several days (2-14), or heated on a steam bath for a few hours, or reflux in a solvent, such as acetonitrile, for a few days (1-3). After the solvent was evaporated the reaction mixture was stirred with acetone causing a crystalline material to separate. The crude product thus obtained was generally purified by dissolving it in a solvent, such as acetonitrile, treating the solution with decolorizing charcoal, removing the charcoal by filtration, and adding a solvent, such as ethyl acetate, until the solution becomes turbid. On standing at room temperature for a few hours a crystalline precipitate gradually formed, which was collected and dried.

The white crystalline material thus obtained constitutes the new compounds of the present invention which may be represented by the following generic formula:

$$\underset{X^{\ominus}}{\underset{R^1}{\overset{R}{\underset{|}{\overset{|}{N}}}}}\text{-picolinyl-O-C(=O)-N(CH}_3\text{)}_2 \cdots \text{(CH}_2\text{)}_n \cdots \underset{X^{\ominus}}{\underset{R^1}{\overset{R}{\underset{|}{\overset{|}{N}}}}}\text{-picolinyl-O-C(=O)-N(CH}_3\text{)}_2$$

wherein n is 5-16 methylene groups, R, R' are radicals selected from the group consisting of methyl, ethyl, propyl, isopropyl, butyl, benzyl, and X is one equivalent of an anion selected from the group consisting of monovalent or polyvalent anions.

The procedure used for the preparation of the new toxic materials is schematically shown below:

$$\text{picolinyl-O-C(=O)-N(CH}_3\text{)}_2\text{-CH}_2\text{-N(R)(R}^1\text{)} + X\text{-(CH}_2\text{)}_n\text{-X} \longrightarrow$$

-continued

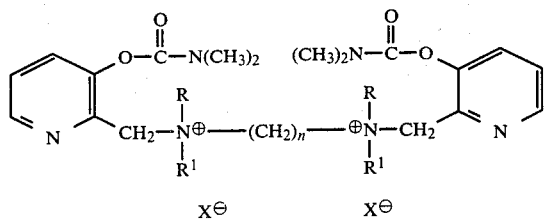

where X is a halide; n and R, R' as defined above.

If compounds are desired in which X is other than a halide ion, the above quaternary compounds are treated with the desired acid by simple exchange reaction as set forth below.

The aminocarbamates were prepared by the Mannich Reaction on 3-pyridol with the desired secondary amines and subsequent carbamoylation of the resultant Mannich bases with dimethylcarbamoyl chloride, schematically shown below:

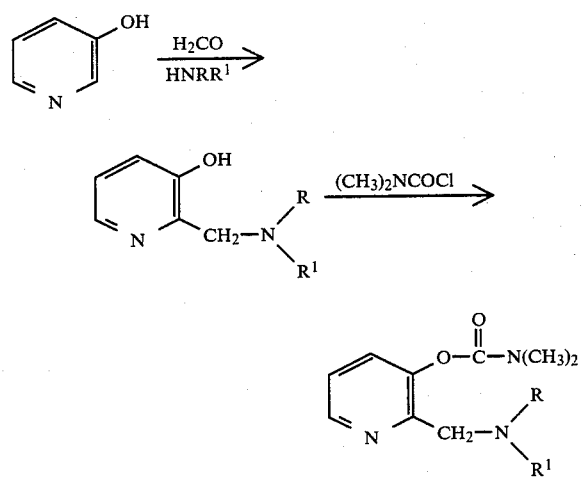

wherein R and R' are radicals selected from the groups consisting of methyl, ethyl, propyl, isopropyl, butyl, and benzyl.

EXAMPLE 1

A mixture of (3-dimethylcarbamoxy-α-picolinyl)-methyl ethylamine (14 gm) and 1,10-dibromodecane (9 gm) was allowed to stand at room temperature for 4 days. During this time, the reaction mixture solidified. After triturating the solid in 100 ml of acetone, the crude product was dissolved in 100 ml of hot acetonitrile, treated with charcoal, and filtered. To the hot filtrate ethyl acetate was added until the solution became turbid. The mixture was then allowed to stand at room temperature overnight. The crystalline white solid that formed was collected and dried to give 8 gm of the product, 1,10-bis[(3-dimethylcarbamoxy-α-picolinyl)ethylamino]decane dimethobromide, m.p. 173°–176° C.

Analysis for $C_{34}H_{58}Br_2N_6O_4 \cdot \frac{1}{2}H_2O$: Calcd: C, 52.2; H, 7.5; Br, 20.4; O, 9.2. Found: C, 52.5; H, 7.5; Br, 19.9; O, 9.3.

| Toxicity IV. $LD_{50}$ | |
|---|---|
| Rabbits | Mice |
| 0.004 mg/kg | 0.011 mg/kg |

EXAMPLE 2

A solution of (3-dimethylcarbamoxy-α-picolinyl)methylethylamine (14 gm) and 1,8-dibromooctane (8 gm) in 150 ml of acetonitrile was refluxed for 48 hours. The solvent was then removed under reduced pressure. 100 ml of acetone was added to the oily residue, and the mixture refluxed for 10 minutes. During this time, the oily material solidified. The solid was separated by filtration and dissolved in 100 ml of hot acetonitrile, treated with charcoal and filtered. To the hot filtrate ethyl acetate was added until the solution became turbid. The mixture was then allowed to stand at room temperature overnight. The crystalline white material that formed was collected and dried to give 3 gm of the product, 1,8-bis[(3-dimethylcarbamoxy-α-picolinyl)ethylamino]octane dimethobromide, m.p. 139°–140° C.

Analysis for $C_{32}H_{54}Br_2N_6O_4 \cdot H_2O$: Calcd: C, 50.3; H, 7.3; Br, 20.9; O, 10.4. Found: C, 50.0; H, 7.1; Br, 20.6; O, 10.1.

| Toxicity IV. $LD_{50}$ | |
|---|---|
| Rabbits | Mice |
| 0.004 mg/kg | 0.006 mg/kg |

The compounds that are representative of our invention are listed below by name and chemical structure.

1,8-Bis[(3-dimethylcarbamoxy-α-picolinyl)ethylamino]octane dimethobromide.

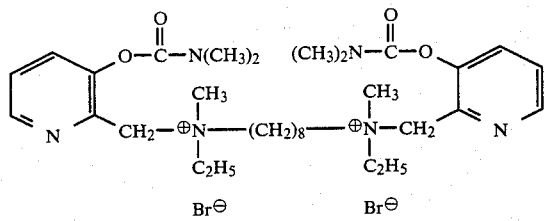

1,10-Bis[(3-dimethylcarbamoxy-α-picolinyl)ethylamino]decane dimethobromide.

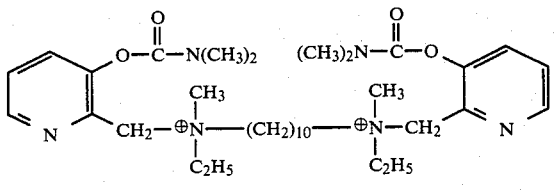

1,10-Bis[(3-dimethylcarbamoxy-α-picolinyl)propylamino]decane dimethobromide.

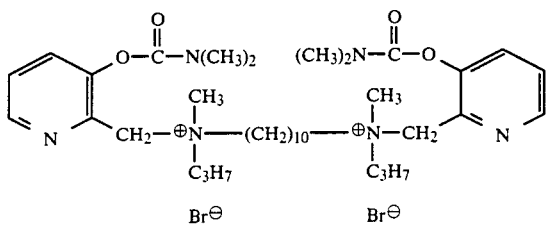

1,8-Bis[(3-dimethylcarbamoxy-α-picolinyl)isopropylamino]octane dimethobromide.

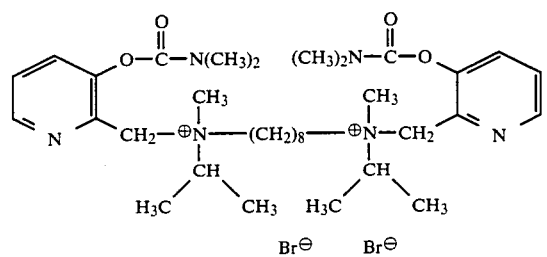

1,10-Bis[(3-dimethylcarbamoxy-α-picolinyl)-butylamino]decane dimethobromide.

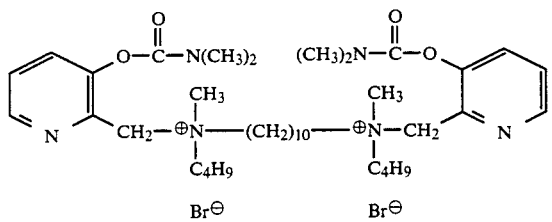

1,10-Bis[(3-dimethylcarbamoxy-α-picolinyl)benzylamino]decane dimethobromide.

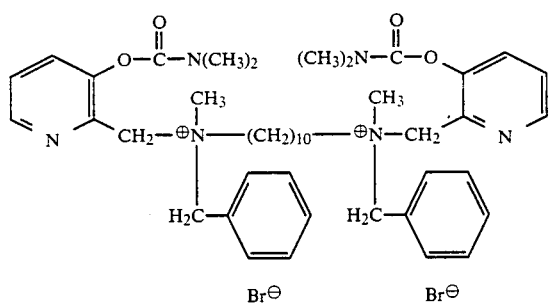

1,10-Bis[(3-dimethylcarbamoxy-α-picolinyl)ethylamino]decane dimethobromide.

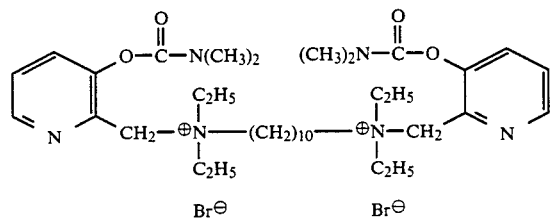

We have shown preferred compounds in which the anion is limited to a halogen, in particular the bromide, since the dibromoalkanes are readily available and are good quaternizing agents. In general, however, it is only necessary that the anions merely have to meet the requirement of being capable of forming a stable salt with the quaternary nitrogens. Thus, the halogen ion can be exchanged with other anions of a relatively strong monovalent or polyvalent acid by conventional methods. For example, if X is a bromide in the quaternary compound, it can be treated with a basic ion exchange resin or mixed with silver oxide and subsequently the desired acid is added. In like manner the hydrogen oxalate, nitrate, perchlorate, and hydrogen sulfate may be prepared.

Representative examples of these additional quaternary salts are:

1,10-Bis[(3-dimethylcarbamoxy-α-picolinyl)ethylamino]decane di(hydrogen methoxalate).
1,10-Bis[(3-dimethylcarbamoxy-α-picolinyl)ethylamino]decane dimethonitrate.
1,10-Bis[(3-dimethylcarbamoxy-α-picolinyl)ethylamino]decane dimethoperchlorate.
1,10-Bis[(3-dimethylcarbamoxy-α-picolinyl)ethylamino]decane di(hydrogen methosulfate).

We claim:

1. A chemical compound having the generic formula:

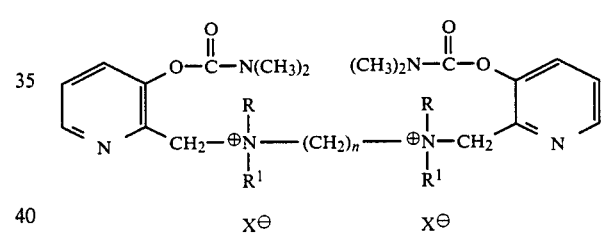

wherein n is selected from 5–16, R, R' are radicals selected from the group consisting of methyl, ethyl, propyl, isopropyl, butyl, and benzyl, and X is one equivalent of an anion selected from the group consisting of halide, hydrogen oxalate, perchlorate, hydrogen sulfate, and nitrate.

2. A chemical compound selected from the group of compounds having the names:

1,8-bis[(3-dimethylcarbamoxy-α-picolinyl)ethylamino]octane dimethobromide;
1,10-bis[(3-dimethylcarbamoxy-α-picolinyl)ethylamino]decane dimethobromide;
1,10-bis[(3-dimethylcarbamoxy-α-picolinyl)-propylamino]decane dimethobromide;
1,8-bis[(3-dimethylcarbamoxy-α-picolinyl)isopropylamino]octane dimethobromide;
1,10-bis[(3-dimethylcarbamoxy-α-picolinyl)ethylamino]decane dimethobromide;
1,10-bis[(3-dimethylcarbamoxy-α-picolinyl)benzylamino]decane dimethobromide.

3. A method of producing a chemical compound having the generic formula:

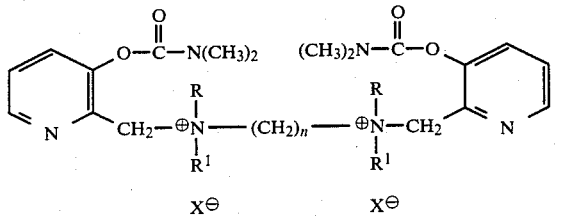

wherein n is selected from 5–16, R, R' are radicals selected from the group consisting of methyl, ethyl, propyl, isopropyl, butyl, and benzyl, and X is the bromide anion, comprising the steps of reacting a solution of (3-dimethylcarbamoxy-α-picolinyl) R amine wherein R is selected from the group consisting of ethyl, propyl, isopropyl, butyl, benzyl, and methylethyl with a an α,ω-dihaloalkane selected from the group consisting of 1,8 dibromodecane and 1,10 dibromodecane; triturating the resultant solid reaction product in solvent; treating the solvent-solid reaction product solution with charcoal; filtering the solvent-solid reaction product-charcoal solution; adding ethyl acetate to the filtrate of the solvent-solid reaction product-charcoal solution to produce turbidity; allowing the filtrate-ethyl acetate to stand at room temperature; and drying the product produced.

4. The process of claim 3 wherein the reacting is by allowing to stand at room temperature.

5. The process of claim 3 wherein the reacting is by refluxing.

6. The process of claim 3 wherein the reacting is by heating on a steam bath.

* * * * *